US00PP30059P2

(12) United States Plant Patent
Dodd et al.

(10) Patent No.: US PP30,059 P2
(45) Date of Patent: Jan. 8, 2019

(54) APPLE TREE NAMED 'MAIA-Z'

(50) Latin Name: ***Malus* x *domestica***
Varietal Denomination: MAIA-Z

(71) Applicant: Midwest Apple Improvement Association, Newcomerstown, OH (US)

(72) Inventors: William Dodd, Newcomerstown, OH (US); David Doud, Wabash, IN (US); John Mitchel Lynd, Pataskala, OH (US); Gregory Miller, Carrollton, OH (US)

(73) Assignee: Midwest Apple Improvement Association, Newcomerstown, OH (US)

( * ) Notice: Subject to any disclaimer, the term of this patent is extended or adjusted under 35 U.S.C. 154(b) by 0 days.

(21) Appl. No.: 15/731,792

(22) Filed: Jul. 31, 2017

(51) Int. Cl.
*A01H 5/00* (2018.01)

(52) U.S. Cl.
USPC ..... Plt./161

(58) Field of Classification Search
USPC ..... Plt./161
See application file for complete search history.

*Primary Examiner* — Annette H Para
(74) *Attorney, Agent, or Firm* — Optima Law Group, APC

(57) ABSTRACT

A new and distinct variety of apple was identified from a population of seedlings derived from a cross of 'Goldrush' and 'Sweet 16'. The new variety, named 'MAIA-Z' is distinct from 'Goldrush' as 'MAIA-Z' ripens late-September, 3 weeks before 'Goldrush'. Unlike 'Goldrush', 'MAIA-Z' has red skin with yellow ground color. 'MAIA-Z' is distinct from 'Sweet 16' as 'MAIA-Z' ripens 2 weeks after 'Sweet 16' and will retain crispness and flavor in normal storage for 20 weeks longer than 'Sweet 16'. The fruit of 'MAIA-Z' adheres to the tree for approximately 6-7 weeks past fruit maturity, while 'Sweet 16' fruit will abscise from the tree within 2 weeks of maturity. 'MAIA-Z' fruit are large sized, crisp, with pleasant sweet-tart flavor and long storability.

3 Drawing Sheets

Latin name: Latin name of the genus and species of the plant claimed: *Malus* x *domestica*.

Variety denomination: Variety denomination: 'MAIA-Z'.

BACKGROUND OF THE INVENTION

A new and distinct variety of apple was identified from a population of seedlings derived from a cross of 'Goldrush' (U.S. Plant Pat. No. 9,392) and 'Sweet 16' (not patented—originating from a cross of 'Northern Spy' and 'Malinda' made in Minnesota, US, and released as a variety in 1973). This cross was made as a part of the Midwest Apple Improvement Association apple breeding project. This superior seedling tree was identified in a population of seedlings from this cross at Belleville, Ill.

The seedling tree was planted as a 1-year-old tree at a commercial orchard in Belleville, Ill., in 2001 and grown among a population of several hundred siblings. Evaluations of fruit quality and tree growth parameters were begun in 2005 and this seedling was identified over several years as superior based upon tree growth habit, precocity, superior fruit quality and harvest time. Utilizing grafting reproduction, the new apple tree variety was asexually propagated by Mitch Lynd at Pataskala, Ohio, and has been observed to remain true to the description set forth herein through successive generations.

The new variety, named 'MAIA-Z' is distinct from 'Goldrush' as 'MAIA-Z' ripens late-September, 3 weeks before 'Goldrush' (FIG. 1). Unlike 'Goldrush', 'MAIA-Z' has red skin with yellow ground color (R.H.S. Color Chart Greyed-Orange 171A with Yellow-Green 151A). 'MAIA-Z' is distinct from 'Sweet 16' as 'MAIA-Z' ripens 2 weeks after 'Sweet 16' and will retain crispness and flavor in normal storage for 20 weeks longer than 'Sweet 16'. The fruit of 'MAIA-Z' adheres to the tree for approximately 6-7 weeks past fruit maturity, while 'Sweet 16' fruit will abscise from the tree within 2 weeks of maturity. 'MAIA-Z' fruit (FIG. 2) are large sized, crisp, with pleasant sweet-tart flavor preferred by a wide range of consumers in blind taste tests.

BRIEF DESCRIPTION OF THE DRAWINGS

The accompanying photographs show typical specimens of the new variety depicted in color as true as is reasonably possible. 'MAIA-Z' photographs were taken in Pataskala, Ohio.

DETAILED BOTANICAL DESCRIPTION

Figure 1:
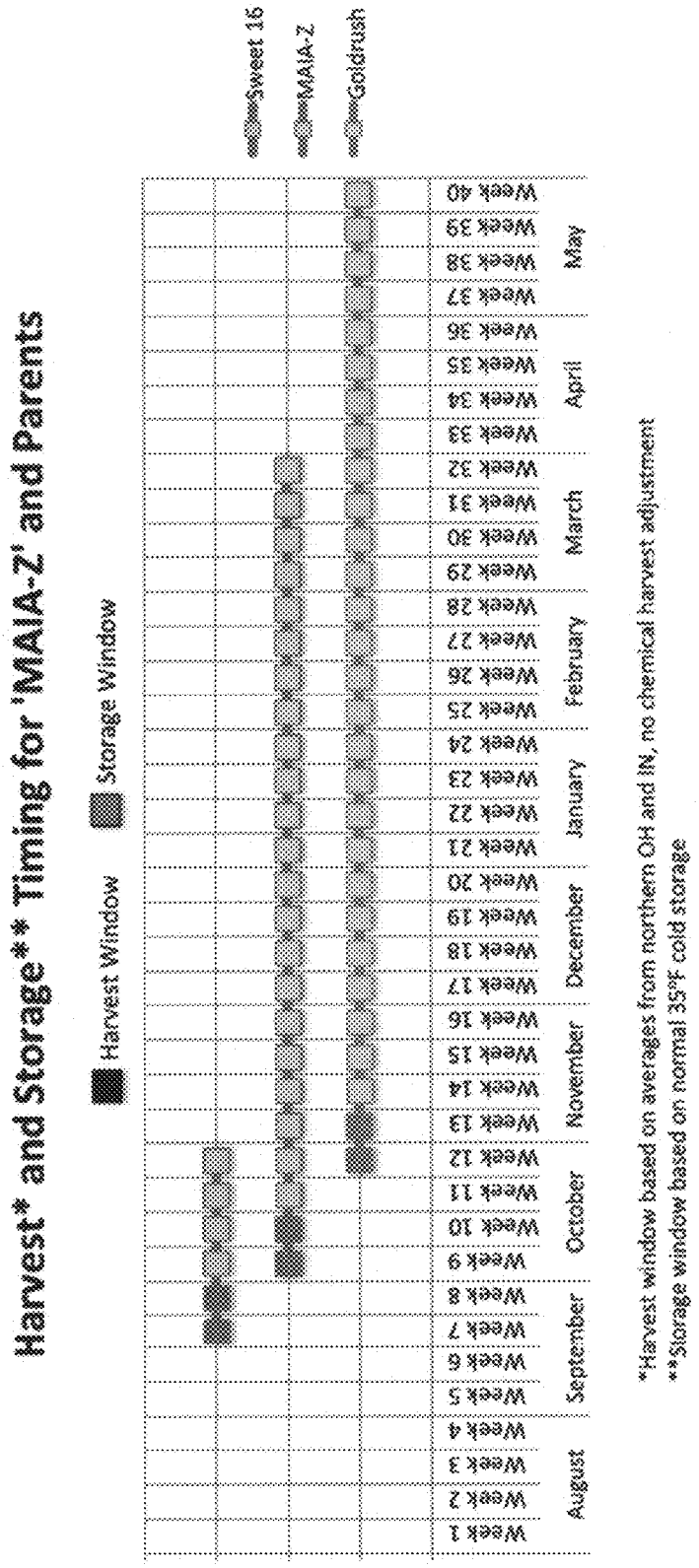
FIG. 1. Shows that 'MAIA-Z' is distinct from 'Goldrush' and 'Sweet 16' in harvest and storage windows.
Figure 2:
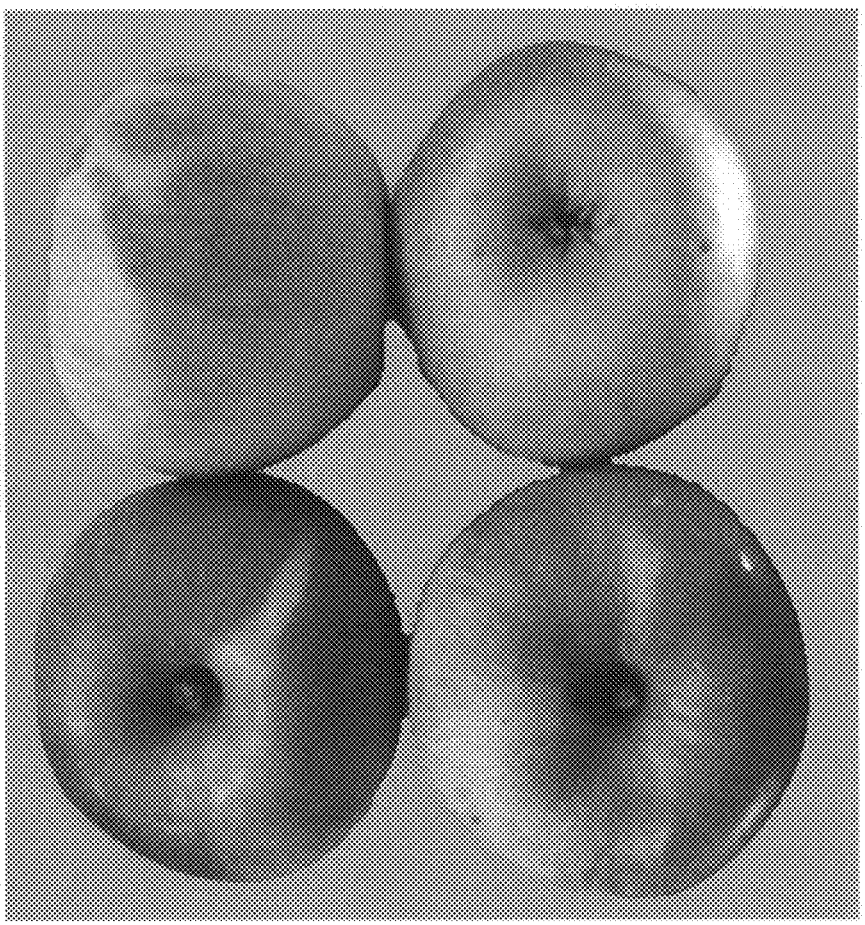
FIG. 2. Typical fruit of 'MAIA-Z' at harvest time.
Figure 3:
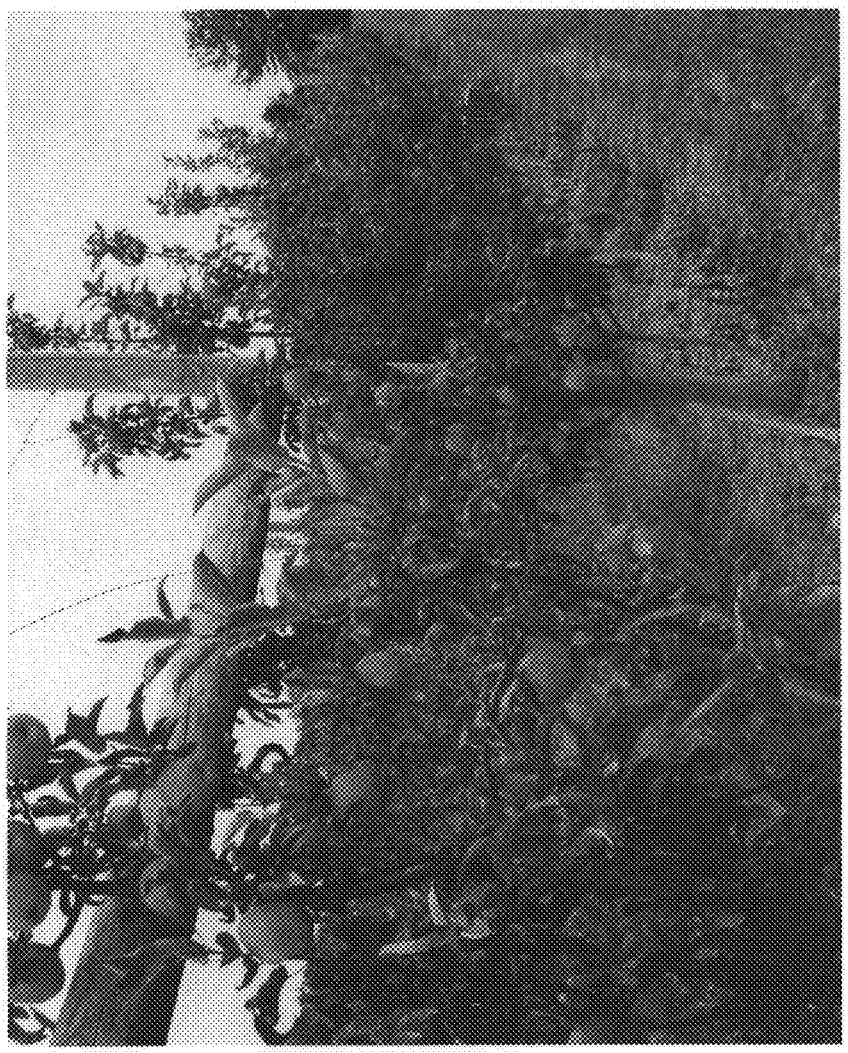
FIG. 3. Typical 'MAIA-Z' trees bearing fruit in September in Ohio.

Color references are made to The Royal Horticultural Society Color Chart (R.H.S.) 2001 Edition.

Parentage: 'Goldrush' female parent and 'Sweet 16' male parent; controlled cross made by Greg Miller in Pataskala, Ohio in 1999.

Grafted tree on b9 rootstock (reference tree):

*Age.*—12 years.

*Size.*—15' height, 8' spread.

*Vigor.*—Medium.

*Form.*—Round, spreading.

*Production.*—Consistently productive.

*Growth type*.—Spindle tree growth form, productive spurs located throughout tree.
*Bearing*.—Annual.

Trunk:
*Reference tree*.—3.5 cm at 15 cm height.
*Bark color*.—Greyed-Brown N199C.
*Lenticels*.—Oblong, 4×1.5 mm.
*Lenticel color*.—Greyed-Brown N199D.
*Lenticel density*.—5 lenticels/cm$^2$.

Branches:
3 *year old*.—10-14 mm in diameter, branch angle 70-80°; Greyed-Brown N199C.
2 *year old*.—8-10 mm in diameter, branch angle 60°; Grey-Brown N199B.
1 *year old*.—5-6 mm in diameter, branch angle 60°; Brown Group 200B.

Leaves:
*Size*.—Length 92-103 mm; width 32-55 mm.
*Texture*.—Leathery, crisp.
*Form*.—Oblong.
*Base*.—Roundly cuneate.
*Apex*.—Acute.
*Adaxial surface pubescence*.—None.
*Abaxial pubescence*.—Fuzzy.
*Adaxial surface color*.—Yellow-Green 146A.
*Abaxial surface color*.—Yellow-Green 146D.
*Veination*.—Pinnate, 10-12 major veins, mainly alternate; Yellow-Green N144D.
*Margin*.—Serrate.
*Petiole length*.—30-35 mm.
*Petiole width*.—2-3 mm.
*Petiole abaxial color*.—Yellow-Green N144D to Greyed-Purple 185B toward base and abscission layer on larger leaves.
*Petiole groove*.—Almost absent.
*Stipules*.—Present but few, very fine like hairs; Greyed-Purple 185B.
*Leaf glands*.—None observed.

Leaf buds:
*Length*.—3 mm.
*Width*.—2-3 mm.
*Color*.—Yellow-Green 149B with Greyed-Purple 187B overtones.
*Placement on branch*.—Alternate.
*Internode distance*.—30-35 mm.

Spurs: Present on 2 yr and older wood.
*Length*.—Varies from 15 to 230 mm.
Relative proportion of spurs of each length.—200-230 mm=2. 100-199 mm=1. 50-99 mm=2. 15-49 mm=7.
*Width*.—5-8 mm.

Flowers at popcorn stage:
*Pedicel*.—Length 3-15 mm; width 1.5-2.5 mm.
*Pedicel color*.—Greyed-Green 191B.
*Bud*.—Length 8 mm; width 10 mm.
*Bud color*.—Purple Group N77B.

Flowers at full bloom:
*Bloom time*.—Blooms with 'Golden Delicious'; bloom time varies with temperature, but is typically during the 4$^{th}$ week of April in northeast Ohio.
*Bloom period*.—Approximately 7 days.
*Presentation*.—Showy.
*Fragrance*.—Aromatic.
*Fertility*.—Fertile.
*Number of flowers per cluster*.—4-6 with 5 typical.

Petals:
*Arrangement*.—Bases not overlapping; 5 petals per flower; each petal 17-20 mm length, 10-12 mm width.
*Color*.—Upper surface (inside) White Group NN155C; Lower surface (outside) slightly colored, White NN155C with shades of Red-Purple 64B.
*Shape*.—Broadly ovate, abruptly cuneate at junction with receptacle.
*Veins*.—Non-distinct.
*Margins*.—Smooth with occasional notching at apex.
*Texture*.—Soft.
*Receptacle*.—Length 4 mm; width 3-4 mm; color Greyed-Green 191B.
*Pedicel*.—Length 11-15 mm; width 4 mm; color Greyed-Green 191B.
*Sepals*.—5/flower; wedge-shaped, sharply pointed; length 5-7 mm; width 4 mm at widest point; adaxial and abaxial color Greyed-Green 191C with Greyed-Purple N186D.
*Stamens*.—12-14 in number.
*Anthers*.—Length 1.5-2 mm; width 0.5-1 mm; color Yellow Group 2D.
*Petal apex*.—Predominantly rounded with some fluting.
*Pollen*.—Present and abundant; color Yellow Group 10C.
*Filaments*.—Length 5-7 mm; width 0.5 mm; color Greyed-Green 157A.
*Pistil*.—Held equal to the anthers in majority of blossoms.
*Ovary*.—Length 3-4 mm; width 2 mm; color Green Group 143A.
*Style*.—Length 8-9 mm; styles are pubescent and fused at base; width 0.5 mm; color Greyed-Green 193D.
*Stigma*.—Width <0.5 mm; held above the anther in the majority of blossoms; color Greyed-Green 197C.

Pollination requirements: Requires cross-pollination from diploid varieties with overlapping bloom; will pollinate diploid varieties of overlapping bloom.

Fruit:
*Maturity when described*.—2 month storage.
*Date of picking*.—Oct. 10, 2016.
*Size*.—Axial diameter 72-91 mm; Transverse diameter shortest point 43-50 mm; Transverse diameter longest point 59-79 mm.
*Fruit weight*.—195-273 g; Average 235 g.
*Form*.—Oblate, conic.
*Cavity*.—Acuminate, deep, russet extends out of cavity.
*Basin*.—Wide, medium depth, wide, corrugated obtuse wavy.
*Calyx*.—Open, medium.

Skin:
*Thickness*.—Medium.
*Tendency to crack*.—Little.
*Stripes*.—Yes, light striping.
*Lenticels*.—Round shape.
*Color*.—Greyed-Orange 171A.
*Ground color*.—Varies between Yellow-Green 151A and Yellow-Orange 18A.

Flesh:
*Aroma*.—Sweet, aromatic.
*Color*.—Yellow-White 158A.
*Texture*.—Crisp, firm, breaking, juicy.
*Eating quality*.—Excellent.
*Flavor*.—Sweet-tart, honeyed citrus.

Core: Medium size.

*Bundle area.*—1184 $mm^2$-2750 $mm^2$.

*Bundle.*—Inconspicuous.

*Axial carpel length:* 9-12 mm.

*Locule.*—Closed.

*Seed cells.*—Walls thin, tough.

Seeds:

*Number perfect.*—5-10.

*Number in one cell.*—1-2.

*Length.*—7-10 mm.

*Breadth.*—4-7 mm.

*Color.*—Greyed-Orange 177A, often covered with white parenchymous tissue.

Stem:

*Length.*—15-35 mm.

*Average length.*—19 mm.

*Width.*—2-3 mm.

*Color.*—Greyed-Green 195A.

Use: Fresh market, dessert.

Shipping quality: Good.

Keeping quality: Good.

Drought tolerance: Average for domestic apple.

Tree winter hardiness: Average for domestic apple.

Disease:

*Resistance.*—Resistant to fireblight (*Erwinia amylovora*) and apple scab (*Venturia inaequalis*).

*Susceptibility.*—Susceptible to powdery mildew (*Podosphaera leucotricha*) and other fungal diseases.

Yield: Approximately 2.5 bushel/tree at 300 trees/acre yields 750 bushels/acre annually.

What is claimed is:

1. A new, distinct apple tree variety named 'MAIA-Z', as illustrated and described herein.

* * * * *